(12) United States Patent
Fredrikson

(10) Patent No.: US 11,369,581 B2
(45) Date of Patent: *Jun. 28, 2022

(54) TWO COMPONENT COMPOSITION

(71) Applicant: ASAMEDIC AS, Oslo (NO)

(72) Inventor: John Bjorn Fredrikson, Elverum (NO)

(73) Assignee: ASAMEDIC AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 17/215,791

(22) Filed: Mar. 29, 2021

(65) Prior Publication Data

US 2021/0212976 A1    Jul. 15, 2021

Related U.S. Application Data

(63) Continuation of application No. 16/311,251, filed as application No. PCT/EP2017/065970 on Jun. 28, 2017.

(30) Foreign Application Priority Data

Jun. 28, 2016    (NO) .................................. 20161073

(51) Int. Cl.
*A61K 31/216*  (2006.01)
*A61K 9/00*    (2006.01)
*A61K 33/00*   (2006.01)

(52) U.S. Cl.
CPC .......... *A61K 31/216* (2013.01); *A61K 9/0053* (2013.01); *A61K 33/00* (2013.01)

(58) Field of Classification Search
CPC .... A61K 31/216; A61K 33/00; A61K 9/0053; A61K 31/616; A61K 47/12; A61K 9/0095; A61K 9/4858; A61P 9/10
See application file for complete search history.

(56) References Cited

U.S. PATENT DOCUMENTS

| | | | |
|---|---|---|---|
| 5,157,030 A | 10/1992 | Galat | |
| 5,776,431 A | 7/1998 | Galat | |
| 7,029,701 B2 | 4/2006 | Chen | |
| 2005/0008690 A1 | 1/2005 | Miller | |
| 2007/0045134 A1 | 3/2007 | Dvorak et al. | |
| 2010/0125242 A1 | 5/2010 | Phykitt | |
| 2012/0316140 A1 | 12/2012 | Phykitt | |
| 2020/0316095 A1 | 10/2020 | Gorbitz | |

FOREIGN PATENT DOCUMENTS

| | | | |
|---|---|---|---|
| CN | 1418635 A | | 5/2003 |
| CN | 101632647 A | | 1/2010 |
| EP | 1428525 A1 | | 6/2004 |
| EP | 2777802 A1 | | 9/2014 |
| GB | 912894 | * | 12/1962 |
| GB | 912894 A | | 12/1962 |
| GB | 1525765 A | | 9/1978 |
| GB | 2321231 A | | 7/1998 |
| WO | 199838104 A1 | | 9/1998 |
| WO | 0066456 A2 | | 11/2000 |
| WO | 200066456 A2 | | 11/2000 |
| WO | 200209666 A1 | | 2/2002 |
| WO | 2004002177 A1 | | 12/2003 |
| WO | 2009007768 A1 | | 1/2009 |
| WO | 2015061521 A1 | | 4/2015 |
| WO | 2017001468 A1 | | 1/2017 |
| WO | 2018002124 A1 | | 1/2018 |

OTHER PUBLICATIONS

Unknown author, title: Heart Attack (Myocardial Infarction); downloaded from https://my.clevelandclinic.org/health/diseases/16818-heart-attack-myocardial-infarction (p. 1), May 19, 2021 (Year: 2021).*
Dressman et al., title: biowaiver monograph for immediate-release solid oral dosage forms: acetylsalicylic acid, Journal of Pharmaceutical Sciences; vol. 101, Issue 8, pp. 2653-2667 Aug. 1, 2012. (Year: 2012).*
Unknown author, Pink Sheet ("Pink", dated Jul. 24, 1989) (Year: 1989).*
Aspirin; from Chemical Stability of Pharmaceuticals, A Handbook for Pharmacists; Kenneth A. Connors, ed.; John Wiley & Sons, New York, pp. 151-160; (1979).
Heart Guard; Product Information Sheet, "Emergency Aspirin Dispenser for Heart Attacks"; 2 pages; printed Dec. 19, 2018; http://dummypage2.tripod.com/.
International Search Report and Written Opinion for International Application PCT/EP2018/086213 International Filing Date: Dec. 20, 2018; dated Mar. 1, 2019; 15 pages.
International Search Report and Written Opinion for International Application PCT/EP2018/086260 International Filing Date: Dec. 20, 2018; dated Mar. 1, 2019; 14 pages.
International Search Report and Written Opinion, International Application No. PCT/EP2017/065970; International Filing Date Jun. 28, 2017; dated Sep. 29, 2017; 13 pages.
Javaid, K. et al.; "Dissolution of Aspirin from Tablets Containing Various Buffering Agents"; Journal of Pharmaceutical Sciences, vol. 61, Issue No. 9; 1972; pp. 1370-1373.
NO 20161073 filed Jun. 28, 2016, NO Search Report, 2 pages.
WHO; "Key Facts"; Cardiovascular Diseases (CVDs); printed Mar. 22, 2019; 6 pages; www.who.int/en/news-room/fact-sheets/detail/cardiovascular-diseases-(cvds).
WHO; "On World Heart Day WO Calls for Accelerated Action to Prevent the World's Global Killer"; printed Mar. 22, 2019; 3 pages; www.who.int/cardiovascular_diseases/en/.
Xian, Y Ed. et al.; "Health Education Prescription of Common Clinical Diseases"; Changjiang Publishing & Media, Hubei Science and Technology Press; 2015; 5 pages.

(Continued)

*Primary Examiner* — Anna R Falkowitz

(74) *Attorney, Agent, or Firm* — Cantor Colburn LLP

(57) ABSTRACT

Described herein is a novel two-component composition including acetylsalicylic acid (ASA) and which is particularly useful in providing an aqueous solution of ASA for immediate peroral administration such as to treat imminent myocardial infarction in a person in need thereof.

16 Claims, 1 Drawing Sheet

(56) References Cited

OTHER PUBLICATIONS

Anonymous; "Phosphate Buffer Calculator"; available online at https://web.archive.org/web/20160229074141/http://clymer.altervista.org/buffers/phos.html [downloaded Aug. 31, 2021]; 2016; 2 pages.

Anonymous; "Trisodium Phosphate"; Wikipedia, available online via the Wayback Machine at "https://web.archive.org/web/20161013211737/https://en.wikipedia.org/wiki/Trisodium_phosphate" [retrieved Aug. 31, 2021]; 2016; 6 pages.

Google Patent Search; "kit comprising aspirin and buffer solution"; patents.google.com, captured Aug. 31, 2021 https://www.google.com/search?q=kit+comprising+aspirin+and+buffer+solution&biw=15; 2021; 2 pages.

Google Patent Search; "two compartment package for incompatible chemicals liquid powder"; patents.google.com, captured Aug. 31, 2021; https://patents.google.com/?q=two+compartment+package+incompatible+chemicals+liquid+powder; 2021; 2 pages.

Google Scholar Search; "Stability of Aspirin in Phosphate Buffer"; scholar.google.com, captured Aug. 30, 2021; https://scholar.google.com/scholar?hl=en&as_sdt=0%2C47&q=stability+of+aspirin+in+phosphate+buffer&btnG=; 2021; 2 pages.

Google Search; "two component aspirin phosphate buffer solution"; google.com, captured Aug. 30, 2021; https://www.google.com/search?q=two+component+aspirin+phosphate+buffer+solution; 2021; 2 pages.

Jordan, J. et al.; "pH of Trisodium Citrate Solutions Stored under Customary Laboratory Conditions"; Nature, vol. 161, Issue No. 4085; 1948; pp. 240-241.

Anonymous: Google Search for "solution of aspirin for heart attack," [conducted Jan. 28, 2022]; 2022; 2 pages.

* cited by examiner

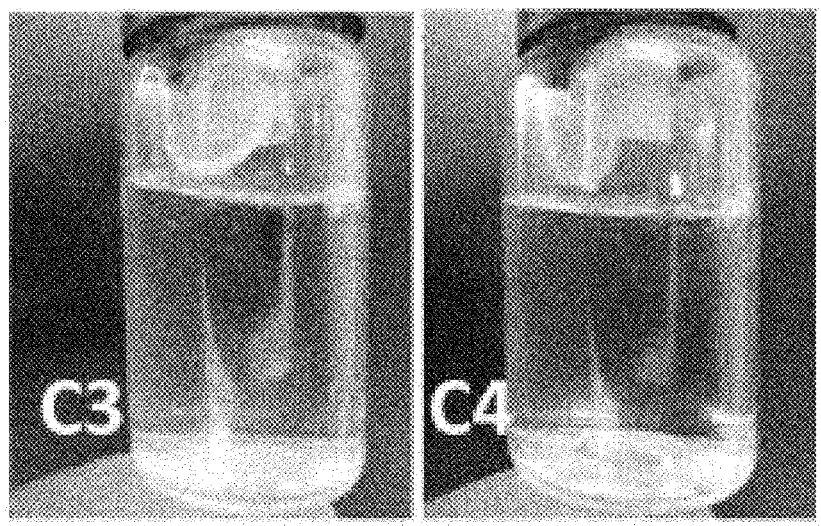

TWO COMPONENT COMPOSITION

CROSS REFERENCE TO RELATED APPLICATIONS

This application is a continuation of U.S. application Ser. No. 16/311,251, filed on Dec. 19, 2018, which is a § 371 National Stage application of PCT/EP2017/065970, filed on Jun. 28, 2017, which claims the benefit of Norwegian Application No. 20161073, filed on Jun. 28, 2016, both of which are incorporated by reference in their entirety herein.

FIELD OF THE INVENTION

The present invention relates to a new two-component composition useful in the treatment and prevention of imminent myocardial infarction. In particular, the invention relates to a pharmaceutical two-component composition, comprising a first component and a second component, wherein the first component comprises acetylsalicylic acid (ASA), and the second component comprises an aqueous solution comprising a salt of an organic acid. The two-component composition enables an immediate dissolution of ASA upon mixing of the first and second components of the present two-component composition, and is in particular useful in the treatment of imminent myocardial infarction. The present two-component composition is in particular useful as a first aid treatment of patients in need for immediate administration of ASA in order to avoid the development of a heart attack, or reduce the extent of damage of a heart attack.

BACKGROUND

Cardiovascular diseases are one of the leading causes of mortality and morbidity in the western world. According to the World Health Organization cardiovascular diseases are the number one cause of death globally, and it is estimated that 17.5 million people die every year from cardiovascular disease, estimated to about 31% of all deaths worldwide. Furthermore, 80% of all deaths by cardiovascular diseases are caused by hearth attacks or strokes.

Although numerous medicinal agents are available for the treatment of the various cardiovascular diseases, such as e.g. cholesterol reducing drugs, numerous medicines aiming at reducing blood pressure, blood thinners, etc., patients with cardiovascular diseases are still at high risk of premature death.

A myocardial infarction (heart attack) is usually heralded by harbingers, i.e., warning signs occurring in advance, making it possible to take action and thus avoid or reduce the serious consequences of a myocardial infarction.

It is well known that chance of survival of patients experiencing symptoms of a myocardial infarction increase significantly if the patients receive ASA as quickly as possible, preferably immediately. Quick administration of ASA is thus crucial in order to avoid death and to reduce damage to the cardiovascular system. To ensure quick absorption and high bioavailability, ASA must be dissolved at the time of administration. ASA however has a poor solubility rendering it difficult to provide an aqueous ASA solution quickly. Further, ASA and salts of ASA hydrolyse rapidly in water (Connors et al., Chemical stability of Pharmaceuticals, A Handbook for Pharmacists, pages 151-160), so it is barely possible to store dissolved ASA.

Hence, in order to successfully treat an upcoming myocardial infarction, a patient needs to have ASA available in a form that can be dissolved quickly and easily and quickly taken by or administered to the patient.

As of today, effervescent tablets containing ASA are commonly used as immediate treatment of patients experiencing symptoms of a heart attack. A product commonly used for this purpose is, e.g. Dispril®, an effervescent tablet containing 300 mg acetylsalicylic acid.

Effervescent formulations in general, as well as those containing ASA, commonly comprise effervescent agents, such as an acid source together with a type of carbonate or hydrogen carbonate, such as sodium hydrogen carbonate or calcium carbonate.

Prior to the administration of the effervescent tablets, the tablets must be dissolved in water, or dissolved in saliva in the mouth of the patient. This might take several minutes, typically 5 minutes.

WO2015/061521 discloses an effervescent tablet comprising high levels of ASA and an alkaline substance (e.g. sodium hydrogen carbonate), and vitamin C.

EP1428525 discloses a pharmaceutical preparation for veterinary use containing ASA in the form of a buffered powder. Said powder still necessitates water in order to dissolve the powder, and will thus not solve the problem of needing to have a glass of water available.

US20120316140 A1 describes a soluble aspirin (=ASA) composition, wherein the soluble aspirin (ASA) composition when introduced to water undergoes a reaction. This reaction triggers effervescing action and the disintegration of the ASA granules which rapidly dissolve in the water.

U.S. Pat. No. 5,776,431 A discloses water-soluble aspirin compositions comprising aspirin, potassium citrate (tri) monohydrate or sodium citrate (tri) dihydrate, and a surface-active agent (e.g. sodium lauryl sulfate). Such a composition comprising 500 mg aspirin is dissolved in 150 ml water.

Multi-compartment capsules comprising different chambers for ingredients with different physical states have been described in US2005008690 A1 and EP2777802 A1. A successful incorporation of ASA into such a capsule is however not disclosed in said document.

The drawbacks with the prior art tablets are that the patients need a glass of water in order to dissolve the tablets, and the complete dissolution may take some time, often too much time.

Furthermore, a patient experiencing signs of an imminent (i.e., developing) myocardial infarction usually has reduced or deficient saliva production, resulting in a dry mouth. Reduced or deficient saliva production is hampering dissolution of an oral tablet containing ASA. It is therefore crucial that the patient has liquid readily available in order to dissolve and/or ingest ASA.

Also, chewable tablets containing ASA are available as immediate treatment of patients experiencing symptoms of a heart attack. However, for the same reason as mentioned above, also the dissolution of and release of ASA from a chewable tablet is often hampered by the reduced or deficient salvia production in the patients.

Taken together, even though products containing ASA for emergency use are available (see, e.g., HEART GUARD™, such products will be inadequate in lack of water or poor saliva production.

There is therefore still a need for an ASA formulation or system suitable for quickly providing an aqueous solution comprising ASA that may be administered to patients in need for urgent treatment of an imminent myocardial infarction. In particular, there is a need for an ASA formulation that avoids the need of additional water or adequate saliva production in a given patient in order for the ASA to be administered and taken up quickly.

SUMMARY

The present inventor has found that a stable ASA formulation can be provided with a two-component system comprising the active ingredient ASA in a first compartment and an aqueous solution of a salt of an organic acid in a second compartment, which upon mixing of the content of the two compartments quickly provides an aqueous solution of ASA that may be administered to or taken by a patient in need thereof.

In particular, a two-component composition is provided comprising a first and a second component, wherein the said first component comprises a therapeutically effective amount of ASA and optionally one or more pharmaceutically acceptable excipients; and wherein the said second component comprises an aqueous solution comprising at least one pharmaceutically acceptable salt of an organic acid and optionally one or more a pharmaceutically acceptable excipient. Said pharmaceutically acceptable excipient of the second component could be a carbonate, such as e.g. sodium carbonate, such as e.g. sodium carbonate anhydride.

In one aspect, said salt of the organic acid is a salt of a tribasic organic acid, such as a salt of citric acid. In yet another aspect, the salt of the organic acid is a monobasic acid, such as a salt of acetic acid or a salt of lactic acid or combination thereof. In yet another aspect, the salt of the organic acid is a salt of a dibasic organic acid, such as a salt of ascorbic acid, a salt of malonic acid, a salt of succinic acid, a salt of glutaric acid or a combination thereof.

According to one aspect, the salt of the organic acid is selected from the group consisting of an alkali metal salt of the organic acid, an alkaline earth metal salt of the organic acid, and a combination thereof. According to yet another aspect, the salt of the organic acid present in the second component of the present two-component system is selected from the group consisting of a sodium salt of the organic acid, a potassium salt of the organic acid and a combination thereof.

In yet another aspect, the second component comprises an aqueous solution comprising a salt of citric acid, such as sodium or potassium citrate.

According to one aspect, the second component of the aqueous solution comprises a salt of a citric acid, such as sodium citrate dihydrate In yet another aspect, the second composition of the two-component composition has a pH of about 8.

In yet another aspect, the second composition of the two-component composition has a pH of about 11.5.

In yet another aspect, the second composition of the two-component composition of the invention comprises a preservative. In one aspect, the preservative is a paraben or benzalkonium chloride.

In one aspect of the present invention, the preservative is selected from the group consisting of methyl paraben, ethyl paraben, propyl paraben, and benzalkonium chloride.

In one aspect of the present invention, the preservative is selected from the group consisting of a salt of methyl paraben, a salt of ethyl paraben, a salt of propyl paraben, and benzalkonium chloride.

In yet another aspect, the second composition comprises in addition to the salt of an organic acid, a salt of a paraben, such as a sodium salt of a paraben.

In yet another aspect, the paraben is selected from the group consisting of sodium methyl paraben and sodium propyl paraben.

According to yet another aspect, a two-component composition is provided wherein the first composition comprises ASA in the range of 100-600 mg.

According to yet another aspect of the invention, the volume of the aqueous solution of the second component is in the range of 6 ml-50 ml. According to one aspect, the volume of the second component is in the range of 10-15 ml.

In one aspect, the two-component composition according to the invention comprises 300-325 mg ASA in the first component and wherein the volume of the second component is in the range of 8-15 ml.

According to another aspect, a two component composition is provided comprising of a) a first component consisting of from 300-325 mg ASA, and b) a second component comprising 10-15 ml of an aqueous solution consisting of 30-50 mg/ml sodium citrate and a preservative selected from the group consisting of sodium methyl paraben, sodium ethyl paraben, sodium propyl paraben and benzalkonium chloride.

The present invention furthermore provides a two-component composition according to the present invention for use in the treatment of imminent myocardial infarction. According to one aspect, the first component comprising ASA is dissolved in the second component comprising the salt of the organic acid, thus providing a ready-to-use aqueous solution of acetylsalicylic acid ASA prior to administration.

According to yet another aspect of the invention, said ready-to-use aqueous solution of ASA is obtained within approx. 2 minutes. In yet another aspect, said ready-to-use aqueous solution is obtained within approx. one minute or less. In yet another aspect, said ready-to-use aqueous solution of ASA is obtained within 0.5-1 minute. According to yet another aspect, said ready-to-use aqueous solution of ASA is obtained in approx. 10-40 sec. According to yet another aspect, said ready-to-use aqueous solution of ASA is obtained within approx. 15-20 sec.

Furthermore, the present invention provides a capsule comprising a first and a second chamber, wherein the first chamber comprises a therapeutically effective amount of ASA and optionally one or more pharmaceutically acceptable excipients; and wherein the said second chamber comprises an aqueous solution comprising at least one pharmaceutically acceptable salt of an organic acid and optionally one or more pharmaceutically acceptable excipient. Said pharmaceutically acceptable excipient of the second component could be a carbonate, such as e.g. sodium carbonate, such as sodium carbonate anhydride.

According to one aspect of the present capsule, the organic acid present in the second chamber is a salt of a tribasic organic acid, such as a salt of citric acid.

According to another aspect the second chamber comprises a salt of a monobasic organic acid, such as a salt of acetic acid or a salt of lactic acid or combination thereof. According to yet another aspect the second chamber comprises a salt of a dibasic organic acid, such as a salt of ascorbic acid, a salt of malonic acid, a salt of succinic acid, a salt of glutaric acid or a combination thereof.

In another aspect, the second chamber comprises an aqueous solution of a salt of citric acid, such as sodium citrate or sodium citrate dihydrate.

In another aspect, the second chamber of the capsule comprises an aqueous solution of a salt of an organic acid having a pH of about 8.

In yet another aspect, the second chamber of the capsule comprises an aqueous solution of a salt of an organic acid having a pH of about 11.5.

In yet another aspect, the second chamber of the capsule further comprises a carbonate, such as e.g. sodium carbonate, such as e.g. sodium carbonate anhydride.

In yet another aspect, the aqueous solution in the second chamber of the capsule further comprises a preservative, such as a paraben, such as a salt of a paraben, such as a sodium salt of a paraben. The second chamber may also comprise benzalkonium chloride as a preservative.

In one aspect, said paraben is selected from the group consisting of sodium methyl paraben and sodium propyl paraben.

Finally, the present invention provides a method for treating imminent myocardial infarction by administering an aqueous solution of ASA to a patient in need thereof, said method comprising the steps of:
a) providing a two-component composition or capsule comprising a first and a second component/chamber according to the present invention;
b) mixing the composition of the first component/chamber comprising a pharmaceutically acceptable amount of ASA with composition of the second component/chamber comprising an aqueous solution of a salt of an organic acid comprised in the second chamber, thus obtaining an aqueous solution of ASA;
c) administering to the person in need thereof the mixture obtained in step b).

According to one aspect, a method is provided, wherein the aqueous solution of ASA obtained in step b) is provided within about two minutes or less, such as about one minute or less.

According to another aspect of the present method, an aqueous solution of ASA is obtained within about 15-20 sec.

BRIEF DESCRIPTION OF THE DRAWING

FIG. 1 shows a picture of device filled with the samples of 3C and 4C of Table 2.

DETAILED DESCRIPTION

Definitions

The term "cardiovascular disease" as used herein refers to diseases where the patients suffering from the cardiovascular disease is in risk of having a heart attack. In particular, "cardiovascular diseases" as used herein includes ischemic heart disease, congestive heart failure, hypertension, valvular heart disease, general atherosclerosis, hypercholesterolemia, etc. The spectrum of ischemic heart disease comprised stable and unstable angina and acute myocardial infarction, conditions usually treated either by pharmacology or by coronary revascularization. Revascularization procedures can be done either catheter-based, or by coronary artery bypass grafting.

The product of the present invention is applicable in the treatment of imminent acute myocardial infarction, where the terms "myocardial infarction" and "heart attack" are used interchangeably herein.

The terms "treating" or "treat" as used herein refers to reduction in severity and/or elimination of symptoms, prevention of the (further) development of a heart attack, and improvement or amelioration of damage that may be caused by a heart attack.

Patients diagnosed with any of the indications listed above may risk developing a heart attack or experiencing symptoms or warnings of a heart attack being imminent. The terms "treatment", "treating" or "treat" as used herein in accordance with the present invention refers to treatment of patients diagnosed with a cardiovascular disease as defined above, and which are in need of ASA due to the occurrence of imminent acute myocardial infarction.

The terms "aspirin" or "acetylsalicylic acid" or "ASA" are used interchangeably herein.

The term "component" as used herein in respect of the first and second component of the present two-component composition refers herein to a component comprising at least one ingredient or compound, and which may also be a mixture of different ingredients or compounds. This is evident from the herein description of the first and the second component of the present invention, e.g. from the fact that the first component comprises ASA and optionally one or more pharmaceutically acceptable excipients, and that the second component comprises an aqueous solution comprising at least one pharmaceutically acceptable salt of an organic acid and optionally one or more a pharmaceutically acceptable excipient.

The term "two-component composition" as used herein refers to a product comprising at least two compositions which are kept apart prior to administration, and which are to be mixed in order to provide a ready-to-use solution to be administered to patients in need thereof.

The term "pH regulating agent" or "acidity regulating agents" as used herein refers to a compound added to the first or the second component of the present composition in order to change or maintain the pH of the composition.

The term "preservative" as used herein refers to a substance or a chemical commonly added to pharmaceutical composition in order to prevent microbial growth or decomposition or undesired chemical changes to a product.

The term "sweetening agent" as used herein refers to compounds commonly added to pharmaceutical composition in order to sweeten or mask an unpleasant taste caused by the active ingredient or any of the excipients used in the composition.

The term "flavoring agent" as used herein refers to compounds commonly added to pharmaceutical composition in order to provide a pleasant taste and/or mask an unpleasant taste caused by the active ingredient or any of the excipients used in the composition.

Description

For patients having a heart attack or experiencing symptoms or warnings of a heart attack being imminent, it is shown that administration of ASA taken as soon as possible increases the chances of survival and reduces the risks of developing damage to the cardiovascular system and the heart. The appropriate dosage of ASA for such use is found to be 300 mg, which correspond to the amount of active ingredient in the effervescent tablet Dispril®, cf. Elwood et al, 2001, The Pharmaceutical Journal, 266:315. The Dispril® tablets comprise calcium carbonate, corn starch, citric acid, talk, saccharine and sodium laurylsulphate.

The problem with the standard prior art tablets containing ASA such as, e.g. Dispril®, is that they firstly must be dissolved in water, and thus necessitate that a glass of water be available whenever needed. In addition, the lack of saliva in the mouth in patients suffering from an imminent heart attack, for reasons of acute fear and adrenergic reactions, results in the patients having trouble to dissolve tablets in their mouth. In both scenarios, this results in the need of water, which is a drawback for swift administration. In addition, the time taken for the prior art tablets to be dissolved, results in the fact that the patients in need of immediate administration of ASA are not provided with said medication quickly enough.

The present invention solves this problem by providing a product that ensures rapid dissolution of ASA and provides a solution that can be quickly administered to the patient, independent of whether a glass of water is available or not and independent of saliva production of the patient.

Acetylsalicylic acid (ASA) is commonly known as aspirin, having the following structure:

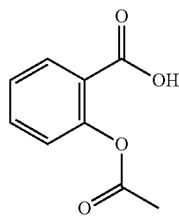

ASA is assigned the CAS Registry number 50-78-2. Aspirin is used in the treatment of numerous conditions, e.g. as analgesic, in treatment of inflammatory disorder, cardiovascular disorder etc. In particular, it is used in order to reduce the risk of death from heart attack. ASA however has poor water solubility, and the low solubility of ASA renders it difficult to provide quickly a solution to be administered when patients is at immediate risk of having a heart attack. In standard pharmaceutical compositions, ASA is rearranged to a soluble salt upon dissolution of the composition in order to improve solubility. Both ASA and the salt of ASA are unstable in aqueous solutions and will quickly hydrolyse forming salicylic acid and acetic acid (Connors et al., Chemical stability of Pharmaceuticals, A Handbook for Pharmacists, pages 151-160).

The present invention provides a two-component composition comprising separately i) a first component composition comprising ASA and optionally one or more pharmaceutically acceptable excipients; and ii) a second component comprising an aqueous solution comprising a pharmaceutically acceptable salt of an organic acid and optionally one or more pharmaceutically acceptable excipients. For example, the second component may comprise an effervescent agent, such as e.g. a carbonate. Typically, carbonates commonly used in effervescence tablets or powder may be used in the second component of the present invention, such as e.g. sodium carbonates or calcium carbonates. According to one embodiment, a pharmaceutically acceptable excipient of the second component is a sodium carbonate, such as e.g. sodium carbonate anhydride.

The two-component composition according to the present invention represents an improvement of emergency treatment of patients having an imminent heart attack, or being in the process of developing a heart attack, in that it provides:
  a ready to use solution comprising ASA,
  Immediate treatment of imminent myocardial infarction without the need of a glass of water,
  Immediate treatment of myocardial infarction independent of saliva production in a given patient,
  a ready to use emergency medicinal product that can be easily carried by a broad population, including patients in risk of developing heart attack as well as their relatives, or being available in first aid kits in private houses or public places as well as emergency rooms at medical practices and hospitals.

Although the present two-component composition is in particular useful as an emergency care product for the treatment of heart attack, the skilled person will acknowledge that the two-component composition may have other useful applications. E.g., aspirin is well known as a painkiller and an antipyretic agent. Thus, the two-component composition of the present invention may also be used for the treatment or prevention of any other medical condition where administration of aspirin to a patient is desired.

According to the present invention, the ASA present in the first composition is quickly dissolved when mixed or added to the aqueous solution comprised in the second composition/compartment.

The aqueous solution comprised in the second composition or compartment of the present invention comprises a salt of an organic acid, such as a tribasic organic acid, such as a salt of citric acid. According to one embodiment, the salt of the organic acid is a monobasic acid, such as a salt of acetic acid or a salt of lactic acid or combination thereof. According to yet another embodiment, the salt of the organic acid is a salt of a dibasic organic acid, such as a salt of ascorbic acid, a salt of malonic acid, a salt of succinic acid, a salt of glutaric acid or a combination thereof.

The salt of an organic acid as used according to the present invention should provide the formation of an easily soluble acetylsalicylate, such as sodium acetylsalicylate or potassium acetylsalicylate. The aqueous solution of the salt of the organic acid should have sufficient buffer capacity in order to slow or counteract the pH reduction affected upon mixture with ASA. According to one aspect, the pH of the aqueous solution of the second component of the present invention has a pH of approx. 8-9, such as 8-8.5. In yet another aspect, the second composition of the two-component composition has a pH of about 11.5.

Without being bound by theory, it is believed that ASA comprised in the first component when mixed with the second component becomes ionized contributing to the quick providing of a dissolution of ASA.

In order to avoid hydrolysis of ASA, the pH of the solution obtained after adding and dissolving ASA in the aqueous solution should be in the range of 5-8. According to one aspect, the pH of the solution obtained upon mixing of the first and the second components of the present invention is approx. 5.2.

In yet another aspect, the solution obtained upon mixing of the first and the second component provides a solution of ASA having a pH in the range of 6.6-7.6, such as in the range of 6.9-7.3. According to one aspect, the pH of the solution obtained upon mixing of the first and the second components of the present invention is approx. 7.1.

The desired pH of the aqueous solution of the second component may furthermore be obtained by including a suitable pH regulating agent.

According to one embodiment, a salt of citric acid is used in the second component, such as sodium citrate. According to another embodiment the salt of citric acid used in the second component is sodium citrate dihydrate (trisodium citrate). The use of a salt of citric acid as the organic acid is furthermore advantage as citric acid also provides a pleasant taste. Thus, if using e.g. sodium salt of citric acid as the organic acid in the second component, further addition of flavoring agents is not necessary.

A further aspect of the present invention is that the dissolution of ASA does not necessitate the use of a surfactant. According to one aspect of the present invention, the second component of the present two-component system comprises an aqueous solution comprising at least one pharmaceutically acceptable salt of an organic acid and optionally one or more pharmaceutically acceptable excipients, provided that the one or more pharmaceutically acceptable excipient is not a surfactant. Said pharmaceutically acceptable excipients of the second component could be a carbonate, such as e.g. sodium carbonate, such as e.g. sodium carbonate anhydride.

In order to preserve the aqueous solution comprised in the second composition/compartment of the two-component composition according to the present invention, one or more preservatives are added to the aqueous solution.

Any pharmaceutical acceptable preservative being effective as preservatives at a pH of about 8 may be used. According to one embodiment, parabens are used as preservative in the second component of the present two-component composition.

Parabens (hydroxybenzoates) is a class of preservatives commonly used in pharmaceutical compositions. Parabens are inter alia used in order to prevent growth of microorganisms and are active against a broad spectrum of microorganism. According to one aspect of the invention, parabens applicable as preservatives in accordance with the present invention may be selected from the group consisting of methyl paraben, ethyl paraben, and propyl paraben.

Alternative preservatives besides parabens suitable for use in a two-component composition according to the present invention is preservatives being effective as preservative at a pH in the range of 4-10. A non-limiting example of an alternative preservative that may be used is benzalkonium chloride.

Some parabens may be poorly soluble in water. In order to provide a more convenient and efficient manufacturing process for the preparation of the aqueous solution of the second component of the present invention, an alkali salt of a paraben may be used. A sodium salt of a paraben is particularly applicable.

According to one aspect, the sodium salt of methyl paraben (Nipagin M Sodium™) or the sodium salt of propyl paraben (Nipasol M Sodium™) is used as a preservative in the aqueous solution of the second component of the present composition.

The pH of an aqueous solution of a sodium salt of a paraben will yield a basic solution with pH of about 9. In the presence of a salt of an organic acid, such as citric acid, the pH may be even higher. In that case, the pH may be reduced by adding a pharmaceutically acceptable pH regulating agent, such as e.g. by adding citric acid. Also, other pharmaceutically acceptable pH regulating agent may be used, such as e.g. acetic acid, lactic acid and/or ascorbic acid.

According to one aspect, the aqueous solution of the second component consists of an aqueous solution of sodium citrate, citric acid and at least one alkali salt of a paraben, such as methyl paraben and/or propyl paraben.

According to the present invention, the first component comprises a pharmaceutically acceptable amount of ASA. Said first component may comprise from 50 mg to 2000 mg ASA, such as from 100 mg to 600 mg. For the purpose of treating imminent myocardial infarction or reducing the damages thereof, the first component of the present invention typically comprises from 300 to 325 mg of ASA.

The volume of the aqueous solution of the second component of the present two-component composition depends upon the specific medical indication as well as the size of the device comprising separately the two-components of the composition. Typically, the volume of the second aqueous solution of the second component is within the range 6-50 ml, such as from 6-40 ml, such as from 8-30 ml, such as from 8-20 ml, or any number in-between said ranges. According to one embodiment of the present invention, the volume of the aqueous solution of the second component is in the range of 8-15 ml. According to one embodiment, the volume of the aqueous solution is in the range of 10-12 ml.

According to one embodiment, the first component comprises from 100 to 600 mg ASA, which is to be dissolved in 6-50 ml of the aqueous solution of the second component of the present two-component composition.

According to another embodiment, the first component comprises from 300 mg ASA, and the second component comprises from 8 to 15 ml of the aqueous solution.

According to yet another embodiment, the first component comprises from 300 mg ASA, and the second component comprises approx. 8 ml of the aqueous solution.

According to yet another embodiment, the first component comprises from 300 mg ASA, and the second component comprises approx. 10 ml of the aqueous solution.

According to yet another embodiment, the first component comprises from 300 mg ASA, and the second component comprises approx. 11 ml of the aqueous solution.

According to yet another embodiment, the first component comprises from 300 mg ASA, and the second component comprises approx. 12 ml of the aqueous solution.

According to yet another embodiment, the first component comprises from 300 mg ASA, and the second component comprises approx. 14 ml of the aqueous solution.

According to yet another embodiment, the first component comprises from 300 mg ASA, and the second component comprises approx. 15 ml of the aqueous solution.

According to one embodiment, the present invention provides a two-component compositions comprising a first and a second component, the first component comprising 300-325 mg ASA; and the second component consisting of from 10-15 ml of an aqueous solution consisting of 30-50 mg/ml of a citrate, such as sodium citrate and 1 mg/ml of a paraben, such as methyl-p-hydroxy benzoate.

According to one aspect, a two-component composition is provided comprising a first component comprising ASA in the range of 300-325 mg, and a second component comprising an aqueous solution comprising 30-50 mg/ml of sodium citrate.

According to another aspect, a two-component composition is provided comprising a first component comprising ASA in the range of 300-325 mg, and a second component comprising an aqueous solution comprising about 150 mg/ml of sodium citrate dihydrate.

According to yet another aspect, a two-component composition is provided consisting of a) a first component comprising from 300-325 mg ASA; and b) a second component comprising 10-15 ml of an aqueous solution comprising about 150 mg/ml sodium citrate dihydrate and a carbonate such as sodium carbonate anhydride According to another aspect a two-component composition is provided comprising a first component comprising 300 mg ASA, and the second component comprising an aqueous solution comprising about 50 mg/ml of a salt of citric acid.

The present first and/or second component of the present two-component composition may optionally comprise further pharmaceutically acceptable excipients. For example, flavoring agents may be added in order to provide a pleasant taste and/or mask an unpleasant taste caused by the active ingredient or any of the excipients used in the composition. Non-limiting examples of compounds that may be used for the purpose of providing a certain taste is citric acid, acetic acid and lactic acid, peppermint essence or juice of fruit or berries, such as e.g. blackcurrant juice.

According to one aspect, a flavoring agent is added to the second component of the present two-component composition. For example, peppermint essence may be added to the second component of the present composition, such as, e.g., in the amounts of about 1% (v/v) of the amount of the second component. Alternatively, blackcurrant juice may be added to the second component of the present composition, such as e.g. in the amount of 20% (v/v) of the amount of the second component. Blackcurrant juice may also act as a pH regulating agent.

The present two-component composition may furthermore include sweetening agents in order to improve taste or mask unpleasant taste of the other ingredients in the composition. The skilled person is well known with various sweetening agents commonly used as sweetening agents in pharmaceutical composition. A non-limiting example of a sweetening agent that may be used in respect of the present invention is saccharine sodium. Saccharine sodium may be added to the second component of the present composition, such as, e.g., in the amounts of approx. 0.03 to 0.06% (w/v) of the amount of second component.

The two component composition included in the present invention may be administered to the patient in need thereof using a device or capsule comprising said first component and the second component in separate departments or chambers of a device or capsule. A predetermined amount of the first component and predetermined amount the second component, will upon operation of the device or capsule be mixed and immediately form a ready-to-use solution of dissolved ASA to be taken by or administered to the patient in need thereof.

For example, a capsule for segregated storage of two-component miscible substances as disclosed in WO00/66456 may be used in connection with the present invention for the treatment or prevention of myocardial infarction.

A package for keeping products separated before used as disclosed in WO98/38104 may also be applied for the purpose of present invention.

The skilled person will understand that a device, package or capsule for segregated storage of two-component miscible substances, such as a first component comprising a dry powder comprising ASA and a second component comprising a dissolution solution according to the present invention, may be designed in various ways. It is to be understood that the two-component composition according to the present invention may be placed in any capsule, package or device that will provide immediate dissolution of the ASA comprised in the first component composition upon mixing with the dissolution solution of the second component composition irrespective of the exact design of the capsule, package or device the two-components may be placed in as long as the two-components are separated during storage and prior to use.

The volume of the chamber of the capsule or storage device to be used with the present second component of the two-component composition is in size suitable for storage of an aqueous solution enabling the dissolution of the desired amount of ASA in accordance with the present invention. Similarly, the volume of the chamber of the capsule or storage device to be used with the present first component of the two-component composition of the present invention is in size suitable for storage of the desired amount of the said first component.

EXAMPLES

Example 1

Preparation of a Two-Component Composition, Dissolution of ASA in Water with Citric Acid and a Preservative The following aqueous solutions (test solutions) were prepared by dissolving and mixing citric acid and a preservative in water. The amount of said ingredients is listed in table 1.

TABLE 1

| Test solutions | A | B | C | D |
| --- | --- | --- | --- | --- |
| Methyl-p-hydroxy benzoate | 0.1 g | 0.1 g | 0.1 g | 0 |
| Sodium citrate | 1.0 g | 3.0 g | 5.0 g | 3.0 g |
| Purified water ad. | 100 ml | 100 ml | 100 ml | 100 ml |

Sample D was included in order to test the effect of the presence of the preservative on the dissolution of ASA, and to evaluate whether the presence of a preservative resulted in undesired foaming.

A device as disclosed in WO98/38104 provided by Bormioli Rocco S.p.A., Italy was used for the purpose of testing the dissolution characteristics of the test solutions.

8, 10, 12, and 14 ml of the test solutions A-D, respectively were filled into the container (bottle) of the test device (3 phase kit with PET bottle, Bormioli Rocco S.p.A., Italy). 300 mg ASA was then placed in the powder compartment of the device. The cap comprising the powder compartment and the cutting element was assembled with the container comprising the test solution.

The cap was then turned down until the seal keeping the powder and the solution separately was broken by the cutting element. The cutting of the seal resulted in that the ASA contained in the powder compartment was released into the test solution in the container. The device was then shaken for about 0.5 to 1 minute or more in case not all ASA was dissolved.

The following samples were tested:

TABLE 2

SAMPLES TESTED IN TWO COMPONENT DEVICE

| Sodium citrate mg/ml | Test solution 8 ml | Test solution 10 ml | Test solution 12 ml | Test solution 14 ml |
| --- | --- | --- | --- | --- |
| 10 | 1A | 2A | 3A | 4A |
| 30 | 1B | 2B | 3B | 4B |
| 50 | 1C | 2C | 3C | 4C |
| 30 without preservative | 1D | 2D | 3D | 4D |

The results show that an aqueous solution of a salt of citric acid, also in the presence of methyl-p-hydroxy benzoate, may be used to provide a fast dissolution of ASA. The results furthermore show that sodium citrate should be in excess in order to obtain a pH in the final ASA solution enabling a fast solution of ASA.

In case the pH of the obtained when mixing ASA with the aqueous citric acid solution is to low, ASA will not be sufficiently dissolved within the time needed for providing a quick administration of ASA to the patient. In particular, the results show that test solution C, which upon mixing with 300 mg ASA provided an aqueous ASA solution with a pH of 5.2, showed better dissolution characteristics compared with e.g. test solution A, which upon mixing with 300 mg ASA provided a pH of the obtained ASA solution of 4.1.

Furthermore, the results show that test solutions comprising 50 mg/ml sodium citrate resulted in faster dissolution of ASA compared with the test solutions comprising 10 or 30 mg/ml sodium citrate, respectively.

Finally, the results showed that a volume of the test solution of 10, 12 and 14 ml, respectively, dissolved ASA faster compared with the 8 ml samples of the test solutions. In particular, the samples 3C, 4B, 4C and 4D performed very well and provided dissolution of sufficiently all the ASA within 0.5-1 minute. Dissolution was inspected visually.

The results also showed that the preservative used did not affect the dissolution of ASA, and did not result in any undesired foaming.

FIG. 1 shows a picture of device filled with the samples of 3C and 4C of table 2.

Example 2

Preparation of a Two-Component Composition, Dissolution of ASA in Water with Trisodium Citrate and Carbonate The following aqueous solution (test solution) were prepared by dissolving and mixing sodium citrate dihydrate (trisodium citrate) and sodium carbonate anhydrid in water. The amount of said ingredients is listed in table 3.

TABLE 3

| Test solution | E |
| --- | --- |
| Sodium citrate dihydrate | 150 g |
| Sodium carbonate anhydrid | 10 g |
| Purified water ad. | 1000 ml |

The device used in example 1 (disclosed in WO98/38104 provided by Bormioli Rocco S.p.A., Italy) was used as described in example 1 for the testing of test solution E.

15 ml of the test solution E was filled into the container (bottle) of the test device (3 phase kit with PET bottle, Bormioli Rocco S.p.A., Italy).

The pH of the aqueous sodium citrate dihydrate and carbonate solution was about 11.5. Thus, no preservative is needed.

300 mg ASA was placed in the powder compartment of the device.

After releasing ASA into the test solution by cutting of the seal separating the powder and the solution, the device was shaken for about 30 seconds.

All ASA was dissolved in 10 seconds, and the pH of this obtained mixed solution was about 7.1-7.2.

The invention claimed is:

1. A method of treating imminent myocardial infarction in a person in need thereof, comprising
a) providing a two-component composition, the two component composition comprising
   a first component comprising 100-600 mg of acetylsalicylic acid and optionally one or more first pharmaceutically acceptable excipients, and
   a second component comprising 6-50 ml of an aqueous solution comprising at least one pharmaceutically acceptable salt of an organic acid, and optionally one or more second pharmaceutically acceptable excipients, wherein the organic acid is selected from the group consisting of acetic acid, lactic acid, citric acid, ascorbic acid, malonic acid, succinic acid, glutaric acid, or a combination thereof, and wherein the aqueous solution of the second component has a pH of 8-11.5,
b) mixing the first component and the second component to provide an aqueous solution of acetylsalicylic acid having a pH in the range of 5-8; and
c) perorally administering to the person in need thereof the aqueous solution of acetylsalicylic acid obtained in step b).

2. The method of claim 1, wherein the second component comprises an aqueous solution of a salt of citric acid.

3. The method of claim 2, wherein the salt of citric acid comprises sodium citrate or potassium citrate.

4. The method of claim 1, wherein the second component comprises an aqueous solution of a salt of citric acid and a carbonate.

5. The method of claim 1, wherein the volume of the second component is 8 ml to 50 ml.

6. The method of claim 1, wherein the amount of acetylsalicylic acid in the first component is 300 mg to 325 mg, and wherein the volume of the second component is 8 ml to 50 ml.

7. The method of claim 1, wherein the aqueous solution of acetylsalicylic acid in b) is obtained within two minutes or less.

8. The method of claim 1, wherein the aqueous solution of acetylsalicylic acid in step b) is obtained within 0.5-1 minute.

9. The method of claim 1, wherein the two component composition is in the form of a capsule comprising a first chamber comprising the first component and a second chamber comprising the second component.

10. The method of claim 9, wherein the second component comprises an aqueous solution of a salt of citric acid.

11. The method of claim 10, wherein the salt of citric acid comprises sodium citrate or potassium citrate.

12. The method of claim 9, wherein the second component comprises an aqueous solution of a salt of citric acid and a carbonate.

13. The method of claim 9, wherein the volume of the second component is 8 ml to 50 ml.

14. The method of claim 9, wherein the amount of acetylsalicylic acid in the first component is 300 mg to 325 mg, and wherein the volume of the second component is 8 ml to 50 ml.

15. The method of claim 9, wherein the aqueous solution of acetylsalicylic acid in step b) is obtained within two minutes or less.

16. The method of claim 9, wherein the aqueous solution of acetylsalicylic acid in step b) is obtained within 0.5-1 minute.

* * * * *